US00PP22714P2

(12) United States Plant Patent
Olesen

(10) Patent No.: US PP22,714 P2
(45) Date of Patent: May 8, 2012

(54) HYBRID TEA ROSE PLANT NAMED 'POULPMT007'

(50) Latin Name: ***Rosa* hybrid**
Varietal Denomination: Poulpmt007

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 12/930,439

(22) Filed: Jan. 7, 2011

(51) Int. Cl.
*A01H 5/00* (2006.01)

(52) U.S. Cl. ..... Plt./133

(58) Field of Classification Search ..... Plt./133
See application file for complete search history.

*Primary Examiner* — Annette Para

(57) ABSTRACT

A new garden rose plant of the hybrid tea class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpmt007'.

SUMMARY OF THE INVENTION

The present invention constitutes a new and distinct variety of garden rose plant which originated from a controlled crossing between the female seed parent, an unnamed, non-commercial seedling, and the male pollen parent, also an unnamed, non-commercial seedling.

The two parents were crossed during the summer of 2000 and the resulting seeds were planted in a controlled environment in Fredensborg, Denmark. The new variety, named 'Poulpmt007', originated as a single seedling from the stated cross.

The new variety may be distinguished from its female seed parent primarily by flower color. The seed parent has light pink flowers, while 'Poulpmt007' has orange blend flowers.

The new variety may be distinguished from its male pollen parent by flower color. The pollen parent has light pink flowers, while 'Poulpmt007' has orange blend flowers.

The objective of the hybridization of this rose variety was to create a new and distinct variety for garden use with unique qualities, such as:

1. Uniform and abundant orange blend hybrid tea shaped flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpmt007' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulpmt007' was selected in the spring of 2001 by the inventor as a single plant from the progeny of the aforementioned hybridization.

Asexual reproduction of 'Poulpmt007' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulpmt007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpmt007'. Specifically illustrated in the drawing are:

FIG. 1; Open flowers, flower buds, flower petals detached, reproductive flower parts.

FIG. 2; Mature and juvenile leaves, mature and juvenile bare stems.

DETAILED DESCRIPTION OF THE VARIETY

The following is a description of 'Poulpmt007', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulrim', U.S. Plant Pat. No. 12,465 are compared to 'Poulpmt007' in Chart 1.

CHART 1

| | 'Poulpmt007' | 'Poulrim' |
|---|---|---|
| Petal Count | 20 petals | 25 to 30 petals |
| Flower Diameter | 50 to 60 mm | 100 to 120 mm |
| Genaral Tonality of Flower Color | On open flower Red Group 52B with intonations of Red-Purple Group 58B. | On open flower blend of Greyed-Orange 170C, Orange 29A with intonations of Red Group 39A. |

FLOWER AND FLOWER BUD

Blooming habit: Repeat.

Flower bud:

*Size*.—Upon opening, 30 mm in length from base of receptacle to end of bud. Bud diameter is 15 mm.

*Bud form*.—Ovoid.

*Bud color*.—As sepals unfold, petals are Red-Purple Group 59B.

*Sepal inner surface*.—Color: Yellow-Green Group 147C with strong intonations of Greyed-Purple Group 183C. Surface: Moderate pubescence observed.

*Sepal outer surface*.—Color: Yellow-Green Group 146A. Anthocyanic pigments the color of Greyed-Purple Group 183A observed. Texture: Smooth.

*Sepal Shape*.—Apex: Cirrhose. Base: Flat at union with receptacle.

*Sepal Margin*.—Margins have medium foliaceous appendages on three of the five sepals.

*Sepal size*.—30 mm long by 10 mm wide.

*Receptacle*.—Texture: Smooth. Shape: Broad funnel. Size: 5 mm in height by 11 mm wide. Color: Yellow-Green Group 144B.

*Pedicel*.—Surface: Somewhat rough with small prickles. Length: 50 mm on average. Diameter: 3 mm on average. Color: Yellow-Green Group 144A. Weak anthocyanic pigments the color of Greyed-Red Group 180A observed. Strength: Strong.

Flower bud development: Singularly.

Flower bloom:

*Fragrance*.—None.

*Duration*.—The blooms have a duration on the plant of approximately 10 days. Petals fall cleanly away from plant after flowers have fully matured.

*Size*.—Flower diameter is 50 to 60 mm when open. Flower depth is 55 mm on average.

*Flower shape*.—High centered, semi double, with a high pointed center which is tightly closed.

*Shape of flower, side view*.—Open flowers are flat at the upper portion and concave at the lower portion.

Petalage: Under normal conditions, flowers have 20 petals total (average), 1 to 3 of which are petaloids.

Petal color:

*Upon opening, outer petals*.—Upper surface: Orange-Red Group 33B at the base, blending with Red Group 52B at the middle zone. Red Group 52B at margins. Lower surface: Red-Purple Group 58B at the marginal and middle zones. Blending with Red Group 51A at the middle and basal zone. Red Group 51A at the basal zone.

*Upon opening, inner petals*.—Upper surface: Red Group 52B at the marginal zone, blending with Orange-Red Group 33B at the middle and basal zone. Primarily Orange-Red Group 33B at the basal zone. Lower surface: The base color is Red-Purple Group 58B. An overlay of Red Group 53C at the margins. Basal zone has blended shades of Red Group 51A.

*Basal petal spots, upon opening*.—Upper surface: Yellow Group 5A. Lower surface: Yellow Group 4B.

*After opening, inner and outer petals*.—Upper surface: Red-Purple Group 52C blended with Orange-Red Group 33C at the mid and basal zone. Lower surface: Red-Purple Group 58B blending with Red Group 50B at the basal zone.

*Basal petal spots, after opening*.—Upper surface: Yellow Group 5C. Lower surface: Yellow Group 5C.

General tonality: On open flower Red Group 52B with intonations of Red-Purple Group 58B. No change in the general tonality at the end of the $10^{th}$ day.

Petals:

*Petal reflex*.—Flat.

*Margin*.—Entire and uniform.

*Shape*.—Broad elliptic. Apex shape: Rounded. Base shape: Rounded.

*Size*.—40 to 45 mm (l)×40 to 50 mm (w).

*Texture*.—Smooth.

*Thickness*.—Above average.

Petaloids:

*Quantity*.—1 to 3.

*Shape*.—Asymmetric with an acute base and apex.

*Color*.—Upper surface is Red Group 52B at the marginal zone, blending with Orange-Red Group 33B at the middle and basal zone. Primarily Orange-Red Group 33B at the basal zone. The lower surface is Red-Purple Group 58B. An overlay of Red Group 53C at the margins. Basal zone has blended shades of Red Group 51A. Basal petal spots on the petaloids are, Yellow Group 5A at the upper portion, and Yellow Group 4B underneath.

*Size*.—35 mm long by 12 mm wide on average.

Reproductive organs:

*Pollen*.—None observed.

*Anthers*.—Size: 2 mm in length. Color: Yellow Group 13A. Quantity: 200 on average.

*Filaments*.—Color: Yellow Group 11A. Length: 12 mm.

*Pistils*.—Length: 12 mm. Quantity: 70 on average.

*Stigmas*.—Level in location relative to the length of the filaments and the height of the anthers. Color: Yellow Group 1C.

*Styles*.—Color: Red Group 39B.

Hips: None Observed in the field nursery in Jackson County Oreg.

PLANT

Plant growth: Upright to bushy. When grown as a budded field grown plant on *Rosa multiflora* understock, the average height of the plant is 80 cm and the average width is 70 cm.

Stems:

*Color*.—Juvenile growth: Greyed-Purple Group 183C. Mature growth: Yellow-Green Group 144B.

*Length*.—On average, canes are 35 cm from the base of the plant to the flowering portion.

*Diameter*.—5 mm.

*Internodes*.—On mature canes, there is an average distance of 35 mm between nodes.

*Surface texture*.—Young wood: Smooth. Older wood: Smooth.

Prickles:

*Incidence*.—5 prickles per 10 cm of stem.

*Size*.—Average length of prickles on mature stems is 9 mm.

*Shape*.—Linear at upper surface, concave underneath.

*Color*.—Juvenile prickles: Yellow-Green Group 144B with intonations of Greyed-Red Group 182A. Mature prickles: Greyed-Yellow Group 161B.

Plant foliage: Normal number of leaflets leaves in middle of the stem: 5, leaflets.

*Compound leaf*.—130 mm (l)×100 (w) on average.

*Quantity.*—3 leaves per 10 cm of stem on average.

*Leaf bearing angle to the stem.*—60 degrees.

*Color of mature foliage.*—Upper side: Yellow-Green Group 147A. Lower side: Yellow-Green Group 147B.

*Color of juvenile foliage.*—Upper side: Greyed-Purple Group 187A. Lower side: Greyed-Purple Group 187B.

Plant leaves and leaflets:

*Stipules.*—Size: 23 mm in length. Quantity: 2 per compound leaf. Shape: Linear, slightly broad based with outward extending apecies. Margins: Entire with few stipitate glands. Color: Yellow-Green Group 146A.

*Petiole.*—Length: 25 mm on average. Diameter: 2 to 3 mm.

*Upper surface.*—Color: Yellow-Green Group 146A.

*Lower surface.*—Color: Yellow-Green Group 146C.

*Rachis.*—Length: 30 mm on average.

*Upper surface.*—Color: Yellow-Green Group 146A.

*Lower surface.*—Color: Yellow-Green Group 146C.

*Leaflet.*—Edge: Serrated. Size: Average size of the terminal leaflet on normal leaves is 75 mm in length by 42 mm wide. Shape: Elliptical. Base: Acute. Apex: Acute. Texture: Smooth. Thickness: Thick. Arrangement: Odd pinnate. Venation: Reticulate. Glossiness: Moderately glossy.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the hybrid tea rose class named 'Poulpmt007', substantially as illustrated and described herein, due to its abundant orange blend flowers, disease resistance, and extended period of bloom.

* * * * *

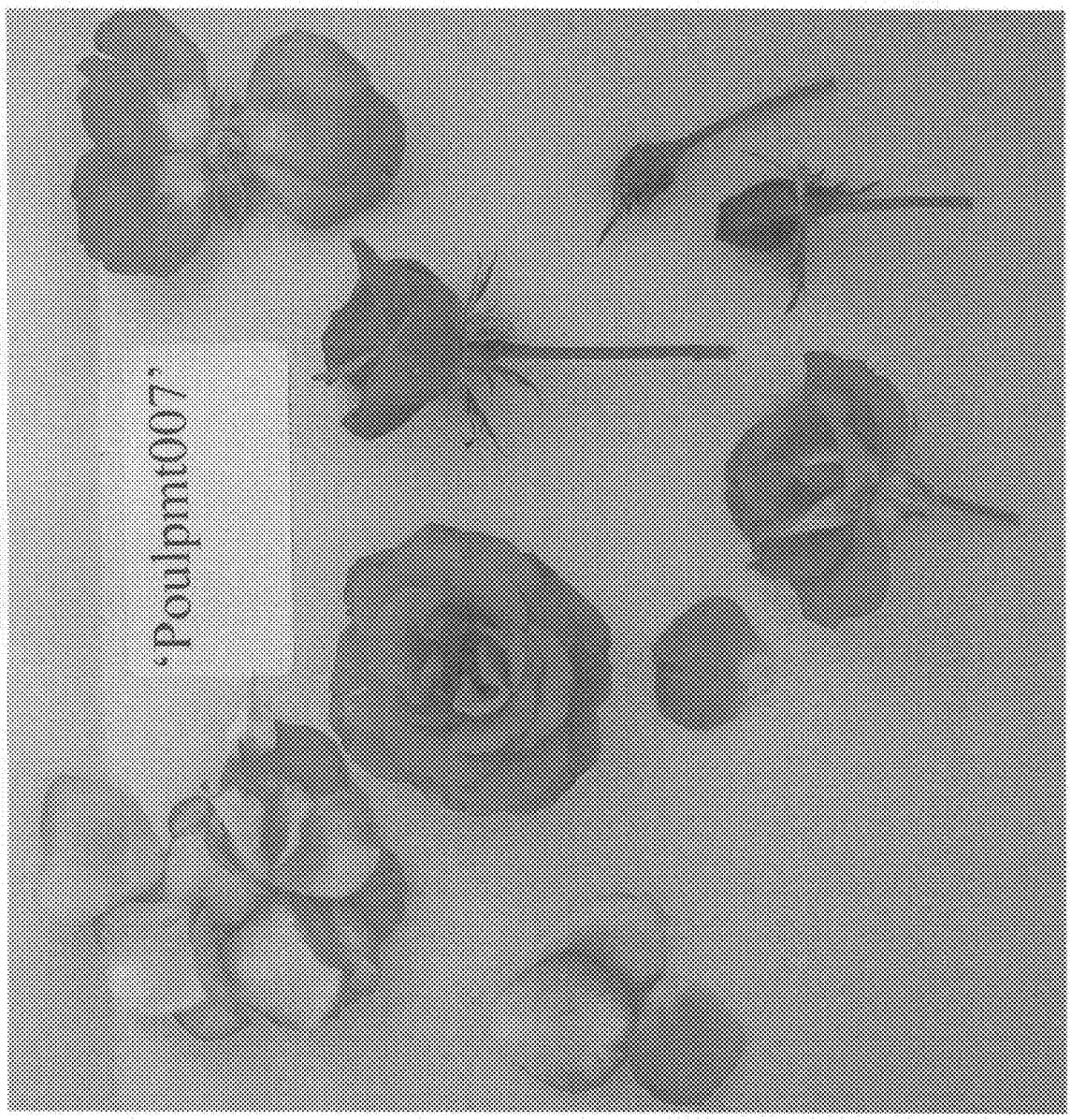
'Poulpmt007'

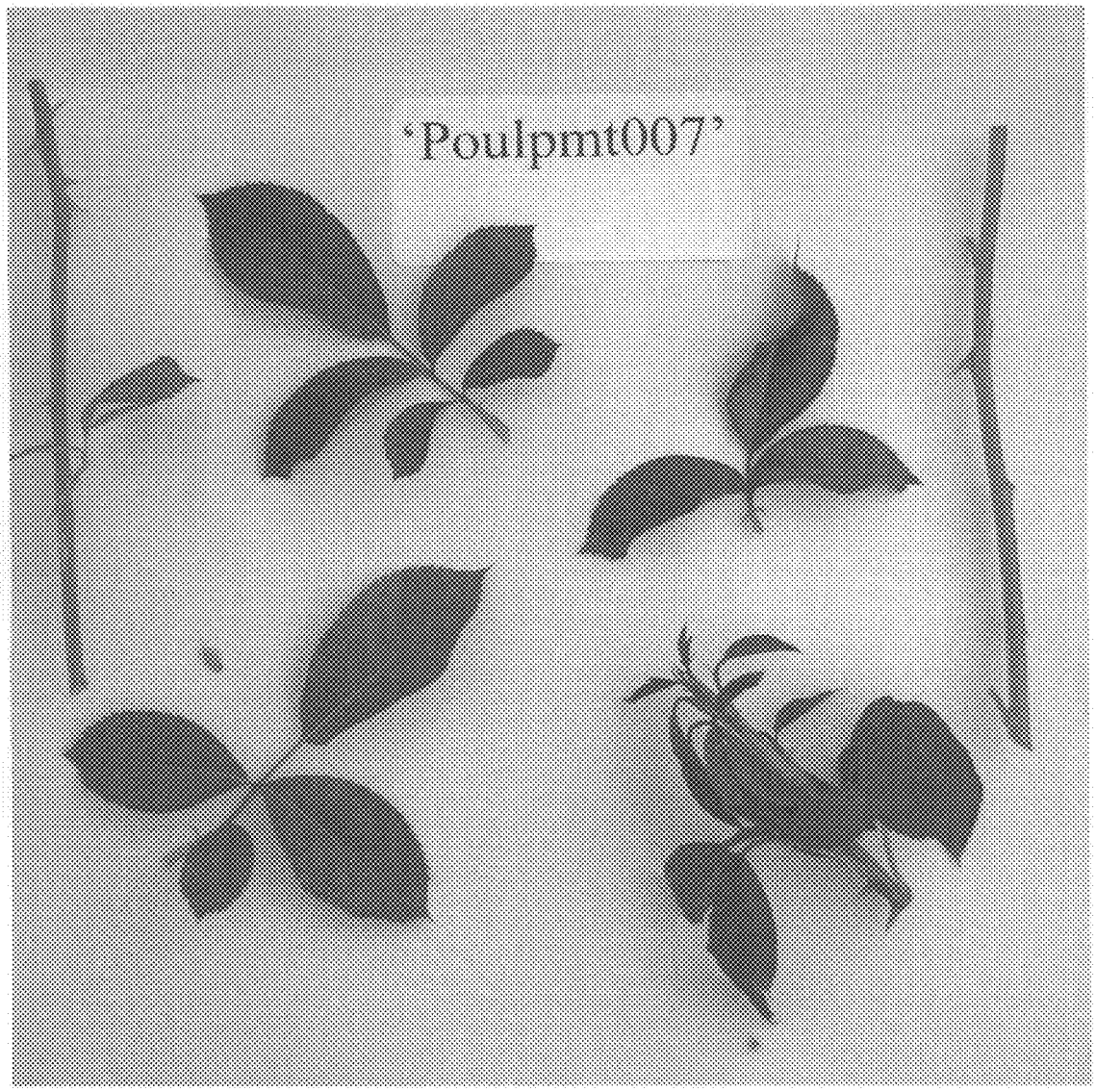
'Poulpmt007'